US012753106B2

(12) United States Patent
Chillon et al.

(10) Patent No.: US 12,753,106 B2
(45) Date of Patent: Oct. 6, 2026

(54) APPARATUS FOR FORMING A CONE FOR HOUSING A NEEDLE IN A SYRINGE, METHOD FOR MAKING A CONE FOR HOUSING A NEEDLE IN A SYRINGE, AND THE SYRINGE THEREOF

(71) Applicant: STEVANATO GROUP S.P.A., Piombino Dese (IT)

(72) Inventors: Alberto Chillon, Piombino Dese (IT); Fabio Chinellato, Piombino Dese (IT); Fabiano Nicoletti, Piombino Dese (IT)

(73) Assignee: STEVANATO GROUP S.P.A., Piombino Dese (IT)

( * ) Notice: Subject to any disclaimer, the term of this patent is extended or adjusted under 35 U.S.C. 154(b) by 877 days.

(21) Appl. No.: 18/002,744

(22) PCT Filed: Jun. 21, 2021

(86) PCT No.: PCT/IB2021/055449
§ 371 (c)(1),
(2) Date: Dec. 21, 2022

(87) PCT Pub. No.: WO2021/260524
PCT Pub. Date: Dec. 30, 2021

(65) Prior Publication Data

US 2023/0271871 A1 Aug. 31, 2023

(30) Foreign Application Priority Data

Jun. 22, 2020 (IT) ........................ 102020000014869

(51) Int. Cl.
*C03B 23/09* (2006.01)
*A61M 5/28* (2006.01)
*C03B 40/027* (2006.01)

(52) U.S. Cl.
CPC ............ *C03B 23/092* (2013.01); *A61M 5/28* (2013.01); *C03B 40/027* (2013.01)

(58) Field of Classification Search
None
See application file for complete search history.

(56) References Cited

U.S. PATENT DOCUMENTS 2,209,739 A * 7/1940 Meyer ................ C03B 23/0496
65/109
8,215,208 B2 * 7/2012 Blackston ............ B25B 13/481
81/177.75
2019/0144326 A1 5/2019 Glacki et al.

FOREIGN PATENT DOCUMENTS

CN 1771065 A 5/2006
CN 201333232 Y 10/2009
(Continued)

OTHER PUBLICATIONS

TW I282779 machine translation, Wang, Kun-Chih, Molding Core for Molding Glass, Jun. 2007 (Year: 2007).*
(Continued)

*Primary Examiner* — Queenie S Dehghan
(74) *Attorney, Agent, or Firm* — Armstrong Teasdale LLP

(57) ABSTRACT

An apparatus for forming a housing cone of a needle in a syringe body of a glass syringe is provided. The apparatus has a forming tool configured to make a hole for creating the housing cone, and a lubricant-coolant liquid dispensing device. The forming tool has a grip portion, a tip, and a tip body, interposed between the tip and the grip portion, suitable for making the hole. The grip portion, the tip body and the tip are in one piece and aligned along a prevailing extension axis. The tip body, with respect to a cross-sectional plane perpendicular to the prevailing extension axis, has a non-circular cross section, inscribed within the maximum circle having as its radius the maximum distance
(Continued)

between a point of the cross section and the prevailing extension axis, measured on the cross-sectional plane.

14 Claims, 4 Drawing Sheets

(56) References Cited

FOREIGN PATENT DOCUMENTS

| | | |
|---|---|---|
| CN | 104363889 A | 2/2015 |
| CN | 107949546 A | 4/2018 |
| CN | 108601898 A | 9/2018 |

OTHER PUBLICATIONS

JP H08157224 machine translation, Yoneda Yashuhiro, Optical Element Forming Die, Jun. 1996 (Year: 1996).*
International Search Report and Written Opinion for International Patent Application No. PCT/IB2021/055449, mailed Oct. 15, 2021, 13 pages.

* cited by examiner

2/4

28
32
36
40
44
48
52
P 28
32
36
40
44
48
P

APPARATUS FOR FORMING A CONE FOR HOUSING A NEEDLE IN A SYRINGE, METHOD FOR MAKING A CONE FOR HOUSING A NEEDLE IN A SYRINGE, AND THE SYRINGE THEREOF

CROSS-REFERENCE TO RELATED APPLICATION

This application is a National Stage Application of International Patent Application No. PCT/IB2021/055449, having an International Filing Date of Jun. 21, 2021, claiming priority to Italian Patent Application No. 102020000014869, having a filing date of Jun. 22, 2020, each of which is hereby incorporated by reference in its entirety.

FIELD OF APPLICATION

The present invention relates to a device for forming a cone for housing a needle in a syringe, a method for making the cone for housing a needle in a syringe, and a syringe thereof thus obtained.

PRIOR ART

As is known, glass syringes comprising a hollow cylindrical syringe body, so as to accommodate a medical substance to be injected in solid, suspension, or solution form, are widely used in the medical industry. The injection is through a frontal delivery end via a needle applied therein, itself hollow and in fluid connection with the body cavity.

Internally housed in the cavity is a piston or plunger that is pushed by the user, or by automatic or semi-automatic systems, to allow the injection of a medical fluid, in a known manner.

The forming, on the syringe body, of the cone configured to fix the needle represents a critical step: in effect, the tip of the tool is attached to the syringe body just before closing the rollers and shaping the glass with said rollers. It is therefore necessary to keep the channel that will accommodate the portion of the needle that is attached to said syringe body open, i.e., pervious, in a stage wherein the glass is extremely hot and malleable: obviously this stage is critical because there is a risk that the hole for housing the needle may close easily.

In effect, this shaping must take place in a precise and controlled manner, since it could lead to the formation of cracks on the glass body, which is particularly fragile, and the consequent mechanical weakening. In addition, the hole for housing the needle must be formed with extreme precision to avoid residual or fragmented glass and/or sharp-edged portions that could result in subsequent cracks developing due to the subsequent insertion of the needle into the desired position or seat.

Moreover, it must be kept in mind that the operation of forming the cone for housing a needle in a syringe must also be as fast as possible, since batches of tens or hundreds of thousands of pieces must be processed. Obviously, increasing the forming speed poses greater risks in terms of defects.

Known solutions, in order to keep the housing hole pervious, involve the use of forming tips that comprise tungsten: tungsten is in effect a particularly hard material and resistant to high temperatures as well as to the considerable abrasion and wear that are generated on the tips when in contact with the glass to be formed.

The problem with tungsten is that, while it solves the problem of resistance to abrasion/wear/temperature by allowing a rather rapid forming operation, it is potentially a contaminant of the glass of the syringe. In other words, small amounts of tungsten from the tip are released onto the glass as a result of abrasion and redeposition of its salts and oxides generated by the high glass-forming temperatures. These tungsten derivatives are potentially incompatible with the medicinal substances and formulations contained in the syringe body and may over time alter their therapeutic efficacy.

For this reason, in forming processes using tungsten tips, said tips are used for a limited time (in the range of 2-4 hours) to minimize the release of tungsten compounds onto the syringe body. After that time, the tips must be replaced.

It is also known to use gas, typically nitrogen, blown during the forming stage in order to avoid or limit as much as possible the formation of tungsten oxides due to the oxidation action of the oxygen contained in the air.

However, these solutions are complex and increase the overall process costs.

Alternative forming tips that do not contain tungsten are also known, whereby the problem of formation of tungsten compounds, such as oxides and salts, is prevented upstream. Tips containing silicon nitride are known to be used for this purpose. However, these solutions have some drawbacks and disadvantages.

In effect, silicon nitride tips, although hard and resistant to medium-high temperatures, do not allow for the speeds and working temperatures reached by the equivalent (in terms of size and geometry) tungsten tips.

To at least partially overcome this limitation of temperature resistance, it is known to properly dose a flow of lubricant-coolant fluid at the contact between the glass and the forming tip, in order to lower its working temperature.

In any case, the lubricant-coolant fluid cannot always penetrate effectively and thus lubricate and cool the tip, because the absolute size, i.e., the thickness of the tip, is extremely small.

The result is that with such tips of the prior art, the productive performance of equivalent tungsten tips cannot be achieved or otherwise exceeded.

DISCLOSURE OF THE INVENTION

Thus, there is a need to resolve the cited drawbacks and limitations with reference to the prior art.

In particular, there is a need for providing forming tips for the housing cone of a syringe needle that allow precise, rapid, and reliable forming, that have a functional life not inferior to that of tungsten tips, and that ensure the total absence or strong reduction of the release of compounds on the syringe body, without requiring the costly and complex use of controlled atmospheres (e.g., with inert gas such as nitrogen).

This requirement is satisfied by a forming apparatus and a method for making a cone for housing a needle in a syringe as described and claimed herein.

DESCRIPTION OF THE DRAWINGS

Further features and advantages of the present invention will be more readily understood from the following description of its preferred and non-limiting examples of embodiments, wherein.

Figure 1A:
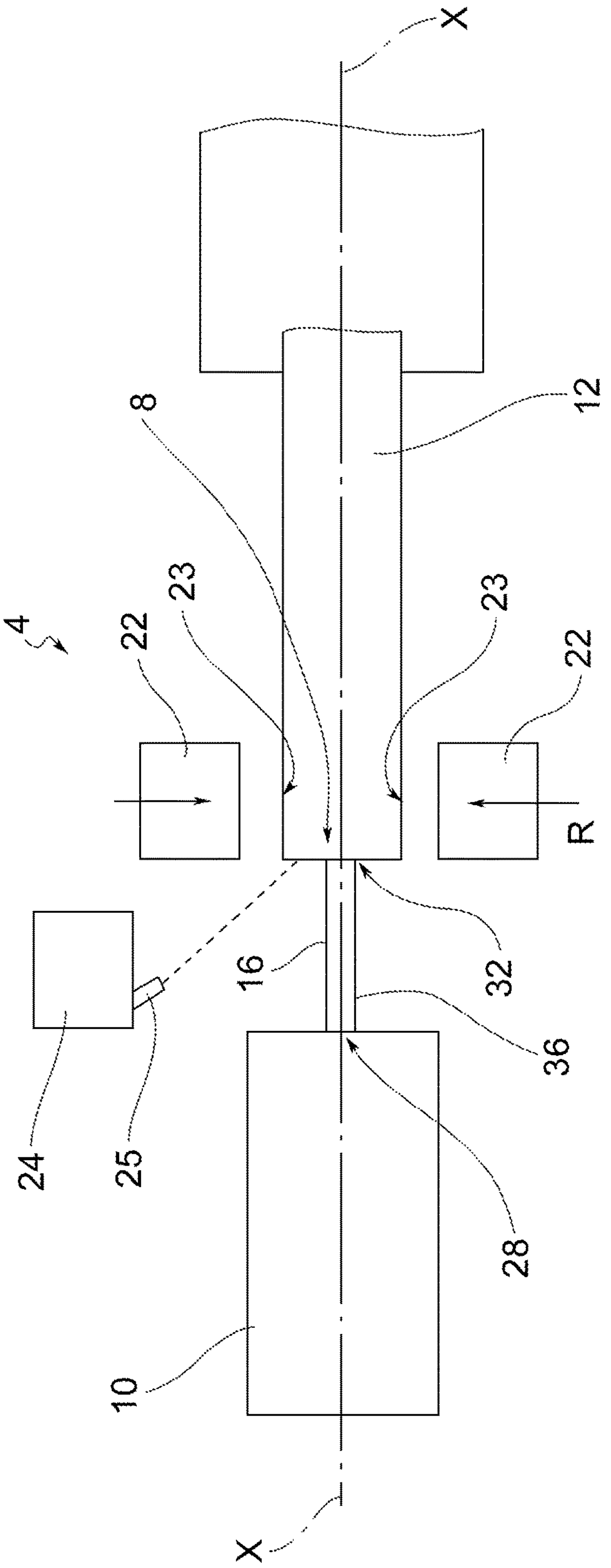
FIG. 1*a* depicts a side view of a forming apparatus according to one embodiment of the present invention.
Figure 1B:
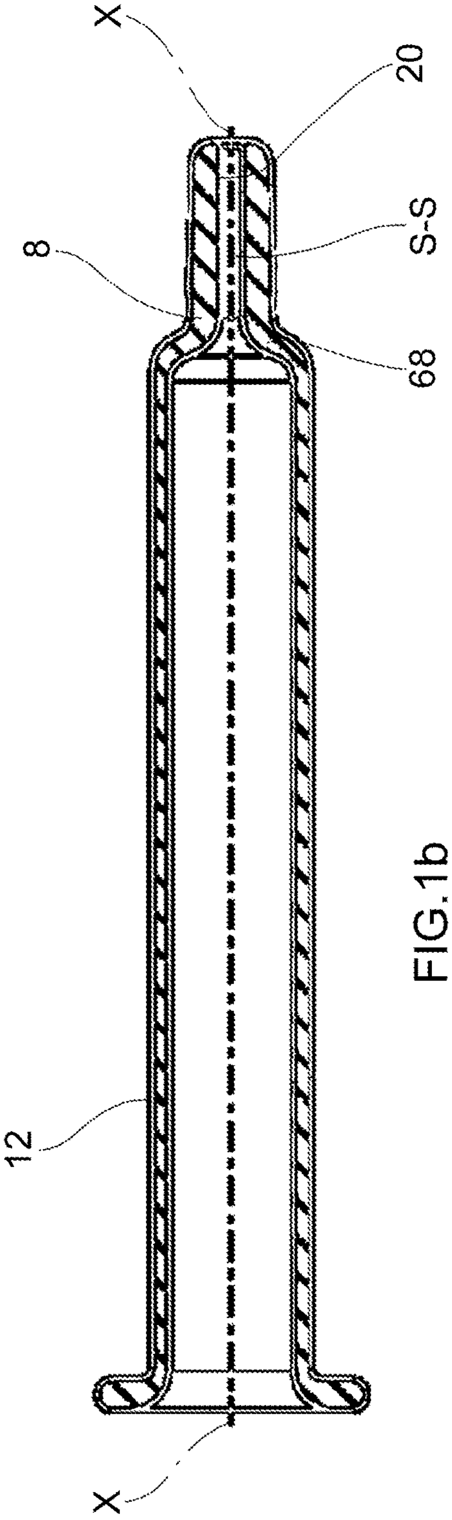
FIG. 1*b* depicts a cross-sectional view of a syringe body formed according to the present invention.

The elements or parts of elements in common among the embodiments described below will be indicated by the same numerical references.

DETAILED DESCRIPTION

With reference to the aforesaid figures, the numerical reference 4 has been used to refer globally to an apparatus for forming the housing cone 8 of a needle in a syringe body 12 of a glass syringe for medical substances. The syringe body 12 has a prevailing extension axis X-X.

The apparatus 4 comprises a forming tool 16 shaped to make a hole 20 for creating said housing cone 8 in the glass syringe body 12.

In other words, the housing cone 8 is obtained in successive stages by forming a wall of said glass syringe body 12 which is shrunk around said forming tool 16, preferably through the use of a pair of rollers 22. Therefore, the forming tool 16 acts as a male plug or pin while the side wall 23 of the syringe body 12 is shrunk thereon by said rollers 22 which move along a radial direction R-R, perpendicular to the prevailing extension axis X-X. Upon removal of the forming tool 16, there will then remain the hole 20 for later housing the needle of the syringe.

The forming apparatus 4 also comprises a lubricant-coolant liquid dispensing device 24 on the tip 32 of the forming tool 16 and/or in the contact area between said forming tool 16 and the glass syringe body 12. The dispensing device 24 may comprise one or more dispensing nozzles 25 of the lubricant-coolant liquid.

For the purposes of the present invention, neither the particular type of dispensing device 24 nor the type of lubricant-coolant liquid used is relevant.

The forming tool 16 comprises a grip or shank portion 28, suitable for gripping by relevant motor means. The motor means may translate, rotate, or roto-translate the forming tool 16 relative to the syringe body 12 along said prevailing extension axis X-X. It is also possible to hold the forming tool 16 stationary and rotate, translate, and/or roto-translate the syringe body 12 along said prevailing extension axis X-X. The forming tool 16 further comprises a tip 32 suitable for forming the syringe body 12, and a tip body 36, interposed between the tip 32 and the grip portion 28, suitable for making said hole 20 by machining the glass.

The grip portion 28, the tip body 36 and the tip 32 are preferably made in one piece with each other and are aligned along a prevailing extension axis as well as a rotation axis X-X of the forming tool 16.

Advantageously, the tip body 36, with respect to a cross-sectional plane perpendicular to the prevailing extension axis X-X, has a non-circular cross section, inscribed within the maximum circle 40 having as its radius the maximum distance between any point P of said cross section and the prevailing extension axis X-X, measured on said cross-sectional plane perpendicular to the prevailing extension axis X-X.

In other words, with respect to the cross-sectional plane perpendicular to the prevailing extension axis X-X, the maximum radius or distance from the same prevailing extension axis is considered, which defines the radius and thus the diameter of the hole 20 that may be made in the syringe body 12 after rotating the forming tool about its prevailing extension and rotation axis X-X.

This means that, with respect to a cross-sectional plane perpendicular to the prevailing extension axis X-X, the cross section of the tip body 36 will always be less than the cross section or area of the maximum circle 40, i.e., the circle having a radius equal to the radius of the hole 20 to be made. In still other words, the tip body 36 has one or more lateral excavations relative to said maximum circle 40.

Preferably, the tip body 36, at its maximum cross section along the prevailing extension axis X-X, has a cross section of less than 85% of the cross section of said maximum circle 40.

According to a further embodiment, the tip body 36, at its maximum cross section along the prevailing extension axis X-X, has a cross section of less than 70% of the cross section of said maximum circle 40.

It is possible to further reduce the ratio between the tip body cross section 36 and the maximum circle 40, so that the necessary mechanical torsional (but also bending) strength of the tip body 36 is always ensured.

In particular, the cross section of the tip body 36 defines, relative to the maximum circle 40, at least one recess 44 suitable to allow the passage of said lubricant-coolant liquid.

In other words, with respect to the theoretical maximum size of the tip body 36 given by the maximum circle 40, it is envisaged to use a geometry that is not circular but instead has at least one recess 44 that constitutes a cavity adapted to form a passage for the lubricant-coolant liquid.

According to one embodiment, the tip body 36, at a cross section along the prevailing extension axis X-X, has a plurality of recesses 44 fluidly connected to each other so as to create a continuous channel for the passage of said lubricant-coolant liquid.

Preferably, the recesses 44 of the tip body 36 are in fluid connection with each other along the prevailing extension axis X-X, so as to create a continuous channel for the passage of said lubricant-coolant liquid along the tip body 36.

The cross section of the tip body 36 is preferably constant along the prevailing extension axis: in other words, the tip body 36 is cylindrical, i.e., consisting of straight lines all parallel to the prevailing extension axis, but having a cross section different from the circular cross section (in particular, smaller than the maximum circle 40 due to the presence of at least one recess 44).

Obviously, for the purposes of mechanical strength and durability/reliability of the forming tool 16, it is preferable for the cross section of the syringe body 36 to be as symmetrical as possible.

It is also possible for the cross section of the tip body 36 to vary along said prevailing extension axis X-X.

For example, according to one possible embodiment, the cross section of the tip body 36 tapers along said prevailing extension axis X-X, moving from the shank or grip portion 28 toward the tip 32.

There are many possible geometries for the tip body 36.

For example, said cross section of the tip body 36 may be a regular polygon, inscribed within said maximum circle 40, such as a triangle, a square, a rhombus, a pentagon, a hexagon, and so forth.

It is also possible for the cross section of the tip body 36 to be a closed polyline, inscribed within said maximum circumference, as in the case of a rectangle, trapezoid, or any closed geometry.

It is also possible to make a cross section of the tip body 36 that is curvilinear, inscribed within said maximum circle 40. This cross section may have straight sides and/or curved sides and so forth.

FIG. 2-14 depict some of these possible embodiments according to the present invention.

As shown by way of example, FIG. 2-14 show some of the possible geometries of the tip body 36 according to variant embodiments of the present invention.

Figures 2A, 2B, 2C, 3A, 3B, 3C, 4A, 4B, 4C, 5A, 5B, 5C:
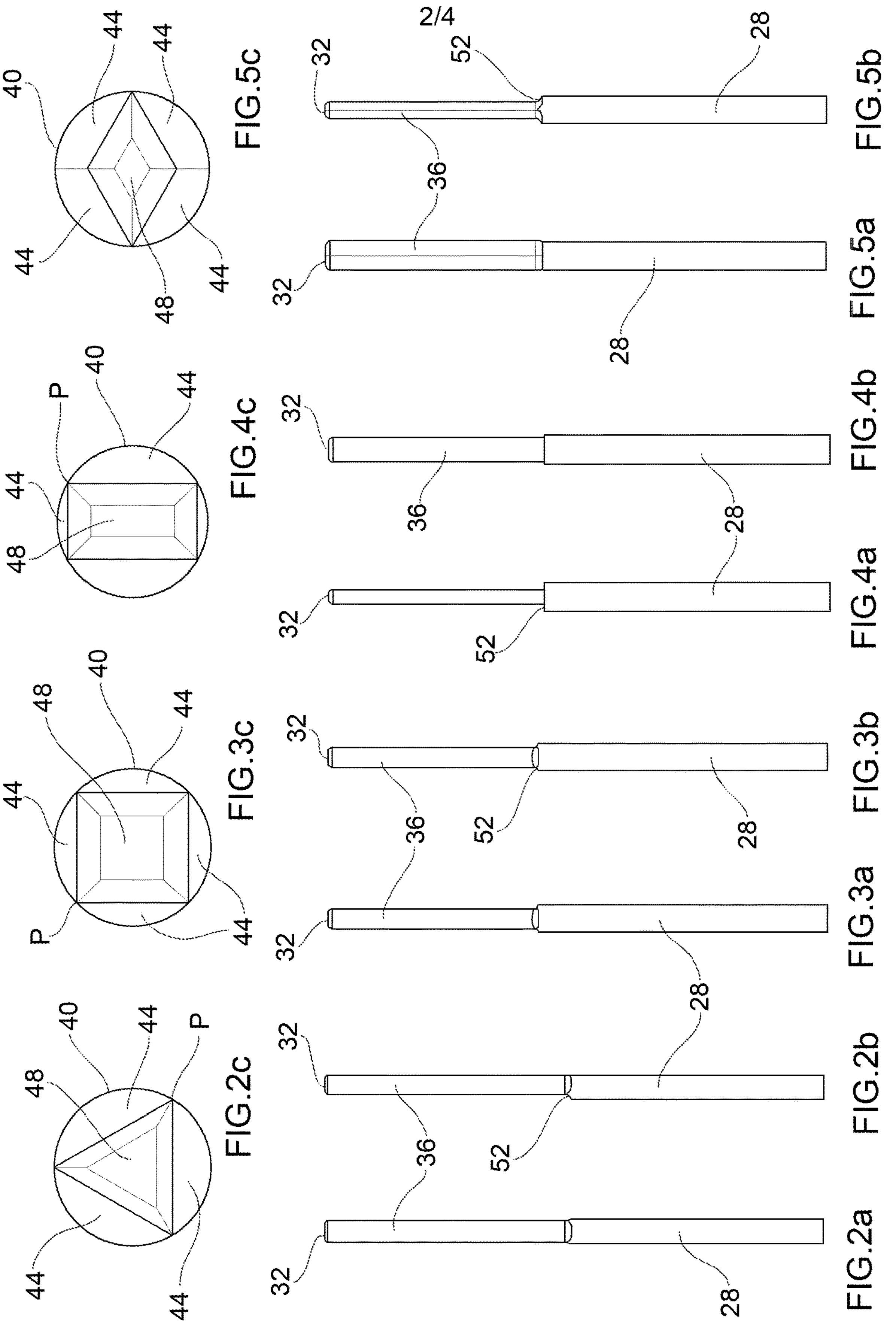
FIG. 2*a*, 2*b*, 2*c* depict respectively two side views and a plan view from the tip side of a forming tool according to a possible embodiment of the present invention.
FIG. 3*a*, 3*b*, 3*c* depict respectively two side views and a plan view from the tip side of a forming tool according to a further possible embodiment of the present invention.
FIG. 4*a*, 4*b*, 4*c* depict respectively two side views and a plan view from the tip side of a forming tool according to a further possible embodiment of the present invention.
FIG. 5*a*, 5*b*, 5*c* depict respectively two side views and a plan view from the tip side of a forming tool according to a further possible embodiment of the present invention.

For example, in FIG. 2*a*-2*c*, a triangular cross-sectional geometry is envisaged, specifically according to an equilateral triangle inscribed in the maximum circle 40.

FIG. 3*a*-3*c* illustrate a square cross-sectional geometry; FIG. 4*a*-4*c* illustrate a rectangular cross-sectional geometry; FIG. 5*a*-5*c* illustrate a rhomboidal cross-sectional geometry.

Figures 6A, 6B, 6C, 7A, 7B, 7C, 8A, 8B, 8C, 9A, 9B, 9C:
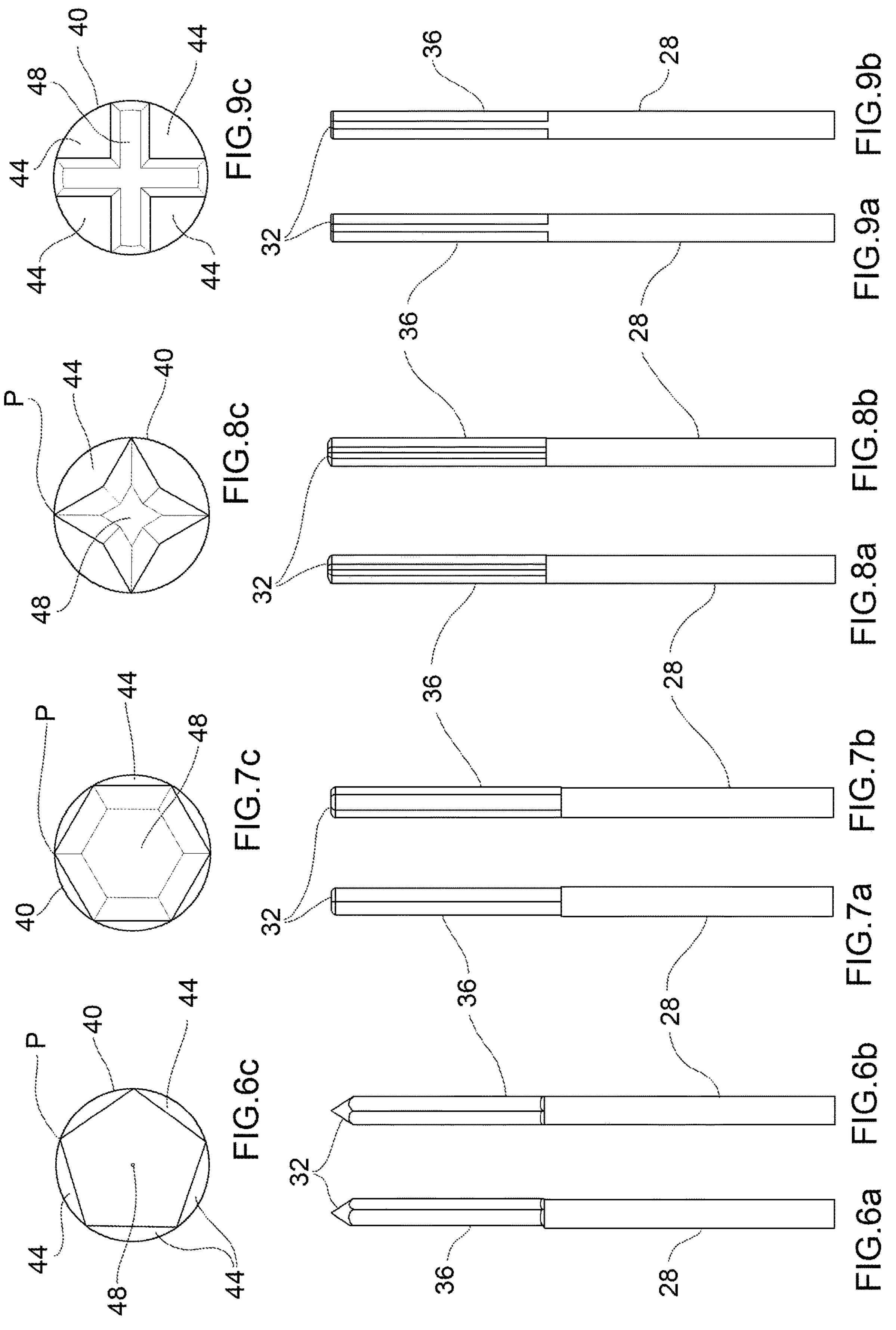
FIG. 6*a*, 6*b*, 6*c* depict respectively two side views and a plan view from the tip side of a forming tool according to a further possible embodiment of the present invention.
FIG. 7*a*, 7*b*, 7*c* depict respectively two side views and a plan view from the tip side, of a forming tool according to a further possible embodiment of the present invention.
FIG. 8*a*, 8*b*, 8*c* depict respectively two side views and a plan view from the tip side of a forming tool according to a further possible embodiment of the present invention.
FIG. 9*a*, 9*b*, 9*c* depict respectively two side views and a plan view from the tip side of a forming tool according to a further possible embodiment of the present invention.

A pentagonal cross-sectional geometry is envisaged in FIG. 6*a*-6*c*, while a hexagonal cross-sectional geometry is envisaged in FIG. 7*a*-7*c*.

FIG. 8*a*-8*c* illustrate a star cross-sectional geometry, while FIG. 9*a*-9*c* envisage a cross-shaped cross-sectional geometry, with arms perpendicular and equal to each other, with a length equal to the diameter of the maximum circle 40.

Figures 10A, 10B, 10C, 11A, 11B, 11C, 12A, 12B, 12C, 13A, 13B, 13C, 14A, 14B, 14C:
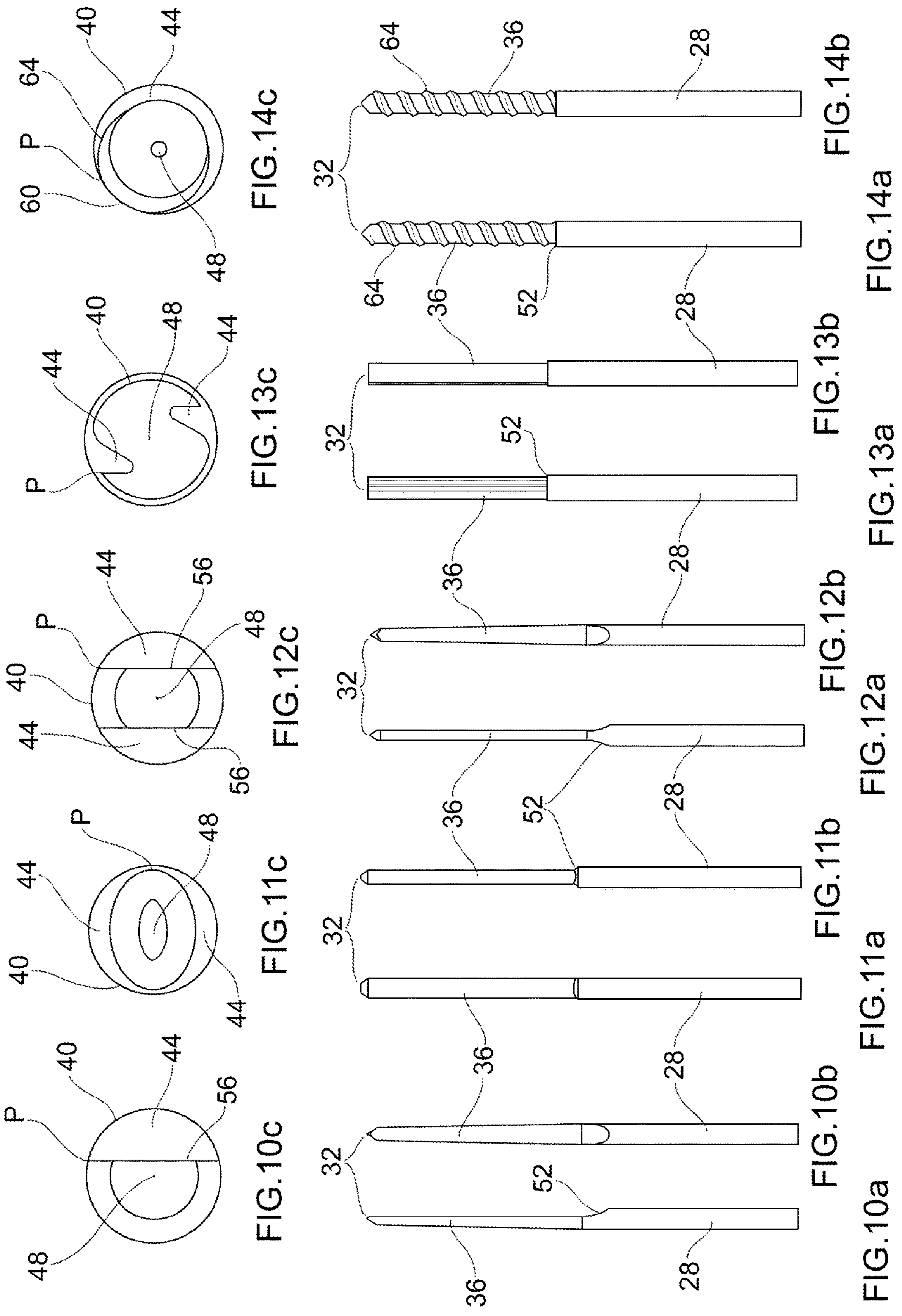
FIG. 10*a*, 10*b*, 10*c* depict respectively two side views and a plan view from the tip side of a forming tool according to a further possible embodiment of the present invention.
FIG. 11*a*, 11*b*, 11*c* depict respectively two side views and a plan view from the tip side of a forming tool according to a further possible embodiment of the present invention.
FIG. 12*a*, 12*b*, 12*c* depict respectively two side views and a plan view from the tip side of a forming tool according to a further possible embodiment of the present invention.
FIG. 13*a*, 13*b*, 13*c* depict respectively two side views and a plan view from the tip side of a forming tool according to a further possible embodiment of the present invention.
FIG. 14*a*, 14*b*, 14*c* depict respectively two side views and a plan view from the tip side of a forming tool according to a further possible embodiment of the present invention.

In FIG. 10*a*-10*c*, a partially circular cross-sectional geometry is envisaged, provided with a facet 56 on one side; preferably, but not exclusively, said facet 56 has an extension less than the diameter of the remaining circular cross section.

In FIG. 11*a*-11*c*, an elliptical cross-sectional geometry is envisaged, wherein the major axis of the ellipse is equal to the diameter of the maximum circle 40.

In FIG. 12*a*-12*c*, a partially circular cross-sectional geometry is envisaged, provided with a pair of facets 56 arranged on opposite, and preferably symmetrical, sides with respect to the prevailing extension axis X-X.

FIG. 13*a*-13*c* illustrate a circular cross-sectional geometry, with a diameter equal to the diameter of the maximum circle 40, provided with a pair of recesses 44, with a substantially parabolic geometry, arranged on opposite sides relative to the prevailing extension axis X-X.

Lastly, FIG. 14*a*-14*c* illustrate a circular cross-sectional geometry, having a diameter less than the diameter of the maximum circle 40, provided with a circular arc 60 substantially tangent to the diameter of said maximum circle 40.

Said circular arc corresponds to a thread 64 that screws as a helix about said circular geometry, along the prevailing extension axis X-X.

The tip 32 is preferably tapered relative to its attachment portion to the tip body 36.

Preferably, said tip 32 has the same geometry as the tip body 36, with respect to a cross-sectional plane perpendicular to the prevailing extension axis X-X.

For example, if the tip body 36 has a square cross section, the tip 32 will also have a square cross section, but tapered, i.e., with a smaller side.

The tip 32 does not need to have sharp ends 48.

For example, the tip may have a flat end 48 contained in a plane perpendicular to the prevailing extension axis X-X.

It is also possible to provide said tip 32 with a conical, pyramidal, or frustoconical end 48.

According to one embodiment, a step or neck-in 52 is provided, relative to a cross-sectional plane perpendicular to the prevailing extension axis X-X, at an area for attaching the grip or shank portion 28 to the tip body 36.

The shank 28 may have any cross section. The shank 28 may even have a circular cross section even equal to said maximum circle 40.

The function of the shank 28 is to allow grasping and/or movement of the forming tool 16 about the prevailing extension axis X-X but does not have the function of removing material from the syringe body 12.

Preferably, the grip or shank portion 28, the tip 32, and the tip body 36 are made of metallic, and/or ceramic, and/or non-metallic material and are tungsten-free.

Obviously, it is also possible to apply the present invention to tips made wholly, or even partially, of tungsten.

As mentioned above, the particular geometry of the forming tool 16 and the tip 32 allows for lubrication and temperature containment at the housing cone 8 whereby contamination of the cone with tungsten compounds (which would easily form at the high temperatures reached with conventional tips) is reduced or the use of ceramic tips with a certain level of breakage resistance is permitted.

However, it was found that by using a ceramic material doped with an yttrium compound, forming tool 16 with a high-strength tip 32 may be obtained. In particular, the combination of this ceramic material doped with yttrium compounds with the geometry of the forming tool 16 and of the tip 32 previously described makes it possible to avoid the use of tungsten tips without losing the characteristics of resistance to high temperatures typical of tungsten tips.

In preferred embodiments, the ceramic material used is silicon nitride ($Si_3N_4$) doped with yttrium oxide ($Y_2O_3$), wherein more preferably the yttrium oxide is contained in the silicon nitride in amounts between 3% and 7% or between 4% and 6% by weight. In certain embodiments, the silicon nitride contains yttrium oxide and alumina ($Al_2O_3$) in a combined amount of between 7% and 13% or between 8% and 12% by weight.

In order to evaluate the residual amount of yttrium present in the cone of a syringe after it has been formed with said forming tool 16 from ceramic material doped with an yttrium compound, analytical detection methods have been developed and are described below.

An analytical method of detecting yttrium is as follows.

Measurement: element Y removable from the syringe cone by extraction in heated ultrasonic bath, with 2% nitric acid (2% $HNO_3$) as extracting solvent;

Analytical technique: Inductively Coupled Plasma-Mass Spectrometry (ICP-MS);

Test item: bulk syringes (not assembled with needle, lacking internal coating), in neutral borosilicate Type I glass (as defined in the USP standard <660>, neutral borosilicate Type I glass), with two types of cone format (Staked Needle—SN—and Luer Lock—LLC);

Quantification Range: 0.1-200 μg/L;

Extractive Methodology:

a) Insert each syringe into a screw-capped test tube b) Fill the syringe with 1 ml of 2% $HNO_3$ and close the tube with its cap c) Immerse in preheated ultrasonic bath for 1 h at 75° C.

d) Shake (with vortex shaker) the test tube with the syringe therein e) Allow to cool to room temperature f) Remove the syringe from the test tube taking care to empty all the liquid in the test tube g) Take 0.3 ml of the extracted solution, transfer it to a new clean test tube, and add 2.7 ml of internal standard solution (Iridium 56 μg/L in 2% $HNO_3$), thus diluting the extract by a factor of 10.

h) Shake the solution to homogenize it.

Instrument Set-Up:

Volume of sample submitted for analysis: 3 mL (obtained by dilution as in step (g))

Use of Internal Standards: Iridium, at a final concentration of 50 μg/L

Mode of acquisition: Standard

Instrument conditioned in 2% $HNO_3$ and calibrated with calibration line for the element Y in the range 0.1-200 μg/L Atomic mass: 193Ir, 89Y;

Calculation of the amount of Y extracted per syringe (considering the extraction volume of 1 mL):

$$Y(ng/\text{syringe}) = C * FD$$

Where C=concentration in the diluted extract (expressed in μg/L) returned by the software FD=dilution factor (equal to 10)

A second method of yttrium extraction from the cone 8 is described below.

Measurement: element Y present in the syringe cone quantifiable following total mineralization/digestion of the glass matrix (only cone area fragment) with the aid of hydrofluoric acid or other solvents propaedeutic to mineralization.

Analytical Technique: Inductively Coupled Plasma-Mass Spectrometry (ICP-MS)

Test item: bulk syringes (not assembled with needle, lacking internal coating), in neutral borosilicate Type I glass (as defined in USP <660>, neutral borosilicate Type I glass), with two types of cone format (Staked Needle—SN—and Luer Lock—LLC);

A third method of yttrium extraction from the cone 8 is described below.

Measurement: element Y present in the syringe cone identifiable by fragmentation of the syringe cone area, subjected to laser ablation for sampling and subsequent determination by ICP-MS without the need for pretreatment or derivatization.

Analytical Technique: Laser Ablation, Inductively Coupled Plasma Mass Spectrometry (LA-ICP-MS)

Test item: bulk syringes (not assembled with needle, lacking internal coating), in neutral borosilicate Type I glass (as defined in USP <660>, neutral borosilicate Type I glass), with two types of cone format (Staked Needle—SN—and Luer Lock—LLC);

Using the methods described above, it has been determined that the yttrium content in the cone of syringes formed with the tip and according to the method of the present invention is between 0.5 ng and 1 ng.

The forming apparatus 4 may include at least one second forming tool shaped for finishing said hole 20 created by means of the forming tool 16.

In other words, the forming apparatus 4 often comprises a plurality of forming tools 16 that have the function of creating the shape of the needle housing cone 8 by successive stages or steps: the first stage consists in the creation of roughing in or formation of the main hole, while subsequent stages are used to define the details. The forming tools 16 used may have the features described above. It is possible that said forming tools 16 have the same shapes but different sizes or that they have different also shapes/geometries/materials. A plurality of forming tools constitute a set of forming tools 16.

The operation or method for forming a cone for housing a needle in a syringe according to the present invention will now be described.

In particular, the forming tool 16 is mounted on a suitable drive means through the shank 28.

Next, the syringe body 12 is rotated about the prevailing extension and rotation axis X-X, taking care to also activate the flow of lubricant-coolant liquid in the area of the tip 32 and/or the tip body 36.

Due to the geometry of the tip body 36, which envisages a smaller cross section than that of the maximum circle 40, the lubricant-coolant liquid allows the glass of the syringe body 12 to be machined, creating the hole 20 and, at the same time, allowing an adequate flow of lubricant-coolant liquid to pass through in order to avoid overheating the forming tool 16 and thus premature wear.

Obviously, the center of the hole 20 (to be made) in the syringe body 12 must be centered or aligned with said prevailing extension axis X-X.

After making the hole 20, the forming tool 16 is extracted and the finishing of the surface of said hole 20 is continued through the use of at least a second forming tool, as described above.

As may be appreciated from that which has been described, the apparatus for forming a cone for housing a needle in a syringe according to the invention enables the drawbacks presented in the prior art to be overcome.

In particular, the present invention makes it possible to avoid or otherwise significantly reduce the release of tungsten compounds on the glass syringe body since it envisages the use of a forming tip that may be entirely tungsten-free.

Thus, the present invention enables a transition from a glass syringe having a low tungsten content (as per solutions of the prior art that make use of tungsten tips and employ techniques to contain the release of tungsten on the glass body), to a glass syringe that is entirely free of tungsten or otherwise contains entirely lower and negligible amounts of tungsten compounds than in the solutions of the prior art.

Despite the absence of tungsten, the forming tip of the present invention allows the same forming precision and speed achievable with a tungsten tip to be obtained, without the use of any controlled atmosphere.

In effect, on the one hand, the absence of tungsten prevents the formation of relevant tungsten compounds and on the other, envisaging a special geometry of the tip body allows the use of an abundant flow of lubricant-coolant fluid so as to effectively control and contain the heating temperature of the tip.

Due to this geometry, there is an adequate cross-sectional passage for the lubricant-coolant fluid that may effectively reach the areas most stressed from a mechanical and thermal point of view, avoiding both the onset of excessive heating and processing imperfections that could generate future cracks in the glass. For example, it is possible to eliminate the so-called "screwing" of the syringe cone surface typical of the methods of the prior art, due to the suboptimal flow of the coolant; this effect manifests itself in an irregular and, in particular, wavy profile of the inner profile of the syringe of the cone; in the case of conventional tips, this effect may in fact be reduced, but not eliminated, only by slowing down the rotation speed, thus slowing down the process consequently.

The mechanical wear of the forming tip of the present invention may also be advantageously monitored and kept under control since the tip is constantly and effectively lubricated and cooled during mechanical processing on the glass body. Therefore, even when using materials less resistant than tungsten, such as silicon nitrides, the tips will still have a reduced consumption and may ensure a high machining precision, since they will never reach critical temperatures due to the presence of effective cooling and lubrication during the mechanical processing of the glass.

In particular, in the case of using a forming tool 16 made of ceramic material doped with an yttrium compound, it is possible to obtain syringes totally free of tungsten (and with an irrelevant residual yttrium content), optimizing at the same time the production process, i.e., providing tips 32 with high strength and durability, which is not possible with ceramic tips of conventional shape and composition.

These syringes are particularly adapted for certain active ingredients sensitive to the presence of tungsten, such as in particular: tocilizumab, Darbepoietin alfa, bevacizumab, Interferon beta 1-alfa, interferon beta 1b, onabotulinum toxin A, exenatide, imiglucerase, certolizumab pegol, glatiramer acetate, secukinumab, triptorelin, dupilumab, etanercept, epoetin, cetuximab, aflibercept, follitropin beta, teriparatide, papilloma virus vaccines, glucagon, FSH—follicolum stimulating hormone, trastuzumab, insulin lispro, Insulin, adalimumab, dibotermin alfa, interferon alfa 2a, paliperidone, pembrolizumab, anakinra, factor VIII—Antiemophilic factor, insulin glargine, enoxaparin, ranibizumab, alemtuzumab, rituximab, tenecteplase, botulinum toxin type A, epoetina beta, pegfilgrastim, filgrastim, somatropin, insulin aspart, activated eptagon alfa, romiplostim, peg aspargase, nivolumab, abatacept, choriogonadotropin alfa, pegilated interferon alfa 2a, pertuzumab, pegilated intefereon beta 1a, *Streptococcus pneumonia* vaccines, denosumab, infliximab, alteplasa, golimumab, basiliximab, eculizumab, ustekinumab, palivizumab, atezolizumab, insulin degludec, ibalizumab, liraglutide, ranibizumab, omalizulab, and pegaspargase.

It is therefore a further subject matter of the present invention to have a syringe filled with one of the aforementioned active substances, characterized in that said syringe does not contain tungsten, and contains a residual amount of yttrium between 0.5 ng and 1 ng.

A person skilled in the art, in order to satisfy contingent and specific needs, may make numerous modifications and variations to the forming apparatus described above, said modifications and variations all being contained within the scope of the invention as defined in the following claims.

What is claimed is:

1. A forming apparatus of a housing cone of a needle in a syringe body of a glass syringe for medical substances, the forming apparatus comprising:

a forming tool configured to form a hole in the syringe body, and at least one dispensing device of lubricant-coolant liquid in a contact zone between said forming tool and the syringe body, wherein the forming tool comprises a grip or shank portion suitable to be gripped and moved by respective motor means, a tip suitable for forming said hole on the syringe body, a tip body, between the tip and the grip or shank portion, suitable for making said hole, and the grip or shank portion, the tip body and the tip being in one piece and aligned along a prevailing extension and rotation axis of the syringe body and/or the forming tool, wherein:

the tip body, with respect to a cross-sectional plane perpendicular to the prevailing extension axis, has a non-circular cross section, inscribed within a maximum circle having as its radius a maximum distance between a point of said cross section and the prevailing extension axis, measured on said cross-sectional plane perpendicular to the prevailing extension axis, such that the tip body has an overall cross section smaller than the cross section of the maximum circle, and the tip and tip body are made of a ceramic material doped with an yttrium compound and are free of tungsten.

2. The forming apparatus of claim 1, wherein the tip body, at its maximum cross section along the prevailing extension axis, has a cross section less than 85% of the cross section of said maximum circle.

3. The forming apparatus of claim 1, wherein the tip body, at its maximum cross section along the prevailing extension axis, has a cross section less than 70% of the cross section of said maximum circle.

4. The forming apparatus of claim 1, wherein the cross section of the tip body identifies, with respect to the maximum circle, at least one recess suitable to allow passage of said lubricant-coolant liquid.

5. The forming apparatus of claim 4, wherein the tip body presents, at a cross section along the prevailing extension axis, a plurality of recesses fluidically connected to each other so as to create a continuous channel for the passage of said lubricant-coolant liquid.

6. The forming apparatus of claim 4, wherein the recesses of the tip body are connected to each other along the prevailing extension axis, so as to create a continuous channel for the passage of said lubricant-coolant liquid along the tip body.

7. The forming apparatus of claim 1, wherein said cross section of the tip body varies along said prevailing extension axis.

8. The forming apparatus of claim 1, wherein the cross section of the tip body tapers along said prevailing extension axis, moving from the grip or shank portion towards the tip.

9. The forming apparatus of claim 1, wherein said cross section of the tip body is a regular polygon, inscribed inside said maximum circle.

10. The forming apparatus of claim 1, wherein said cross section of the tip body is a closed polyline, inscribed inside said maximum circle.

11. The forming apparatus of claim 1, wherein the cross section of the tip body is curved, inscribed inside said maximum circle.

12. The forming apparatus of claim 1, wherein said tip is tapered with respect to an attachment portion thereof to the tip body.

13. The forming apparatus of claim 1, wherein said tip has the same geometry as the tip body, with respect to the cross-sectional plane perpendicular to the prevailing extension axis.

14. The forming apparatus of claim 1, wherein said ceramic material is silicon nitride ($Si_3N_4$) doped with yttrium oxide ($Y_2O_3$), wherein the yttrium oxide is contained in the silicon nitride in amounts between 3% and 7% by weight, or said ceramic material is silicon nitride containing yttrium oxide and alumina ($Al_2O_3$) in a combined amount of between 7% and 13% by weight.

* * * * *